United States Patent [19]

Schmale

[11] Patent Number: 5,051,696
[45] Date of Patent: Sep. 24, 1991

[54] SURFACE TESTING DEVICE WITH RECIPROCATING SENSOR

[75] Inventor: Erhard Schmale, Breuna-Wettesingen, Fed. Rep. of Germany

[73] Assignee: Thyssen Industries AG, Essen, Fed. Rep. of Germany

[21] Appl. No.: 437,368

[22] Filed: Nov. 16, 1989

[30] Foreign Application Priority Data

Nov. 26, 1988 [DE] Fed. Rep. of Germany ....... 3839938

[51] Int. Cl.$^5$ .................... G01N 27/82; G01N 29/04; G01N 21/88; G01R 33/12
[52] U.S. Cl. .................................... 324/262; 73/633; 324/226; 324/227; 324/242; 356/380
[58] Field of Search ............... 324/206, 226, 227, 229, 324/242, 243, 262; 73/618, 627, 628, 633, 634, 641; 356/380, 386, 341

[56] References Cited

U.S. PATENT DOCUMENTS

| 4,258,319 | 3/1981 | Shimada et al. | 324/262 X |
| 4,602,555 | 7/1986 | Bushey | 73/665 X |
| 4,682,498 | 7/1987 | Kreiskorte | 73/618 |
| 4,855,678 | 8/1989 | Krieskorte | 324/262 |

FOREIGN PATENT DOCUMENTS 343134 1/1960 Switzerland .

Primary Examiner—Gerard R. Strecker
Attorney, Agent, or Firm—Michael J. Striker

[57] ABSTRACT

A surface testing device comprising a vibratory system for the reciprocating movement of a sensor carrier (3) arranged above the surface to be tested and comprising an exciter arrangement for operating the system at or in the vicinity of its resonance frequency wherein the vibratory system contains spring elements in the form of pneumatic springs (5, 6) acting on the sensor carrier (3) in opposite directions, which pneumatic springs (5, 6) are pretensioned in the rest state of the system by a magnitude corresponding to at least half of the displacement path of the sensor carrier (3) FIG. 1.

10 Claims, 5 Drawing Sheets

SURFACE TESTING DEVICE WITH RECIPROCATING SENSOR

BACKGROUND OF THE INVENTION

The invention is directed to a surface testing device comprising a base frame, a vibratory system including a sensor carrier and spring elements for reciprocating the sensor carrier and coupled thereto, and an exciter for operating the system in vicinity of its resonance frequency.

Known surface testing devices of this type (U.S. Pat. No. 4,682,498) serve, among other things, to test the surfaces of flat steel slabs, heavy plates or other test pieces for defects or other characteristics by means of sensors which are reciprocated preferably close above the surfaces to be tested. Either an individual torsion spring bar or a pair of torsion spring bars which are excited in the same direction serve as spring elements.

The vibratory systems constructed from such torsion spring bars bring about numerous undesirable problems. For example, the costly work which is required in exchanging defective parts such as the torsion spring bars, their bearings, the sensor carriers or the like, the visual check of the torsion spring bars or their bearings for the purpose of early detection of damages, which visual check is desirable but only possible at high expense, e.g. the disassembly of the system parts, the impossibility of adjusting the zero position of the sensor carrier or the sensors during operation, the high manufacturing costs and outlay caused by the absence of standard structural component parts, particularly torsion spring bars, and the fact that the adjustment of the resonance and natural frequency of the vibratory system to a preselected or prescribed value is only possible by means of re-equipment, the resonance and natural frequency being determined by the vibrating masses and the dimensioning of the torsion spring bars. But, above all, the required large constructional volume, which is a function chiefly of the required minimum dimensioning of the torsion spring bars, is troublesome and in particular results in considerable space related problems in the testing of surfaces of slabs, or the like, from a plurality of sides, since it presents an obstacle to the combination of a plurality of vibratory systems in a single compact surface testing station.

SUMMARY OF THE INVENTION

Therefore, the invention has the object of improving the surface testing device of the generic type named in the beginning in such a way that it can be constructed so as to economize on space and in such a way that the spring elements are installed so as to be easily accessible and exchanged, if necessary, at low cost and can be monitored visually in the course of operation.

The object of the invention is achieved by providing spring elements comprising pneumatic springs acting on the sensor carrier in opposite direction and prestressed in a state of rest of the system by a magnitude corresponding to at least half of the displacement path of the sensor carrier.

The invention includes several considerable advantages. In addition to the simple installation and disassembly, the small constructional volume and the ability to visually monitor the spring elements, pneumatic springs also provide a multitude of possibilities for controlling and regulating in the course of operation, particularly changing the natural frequency of the vibratory system and changing the zero position and/or the vibration amplitude of the sensor carrier and sensors. Finally, the manufacturing, assembly and acquisition costs of the surface testing device, according to the invention, are comparatively low, since standard elements, known per se, can be used as pneumatic springs.

The invention as to its construction so to its mode of operation, together with additional objects and advantages thereof, will be best understood from the following detailed description of the preferred embodiments with reference to the accompanying drawings.

DETAILED DESCRIPTION OF THE PREFERRED EMBODIMENTS

Figure 1:
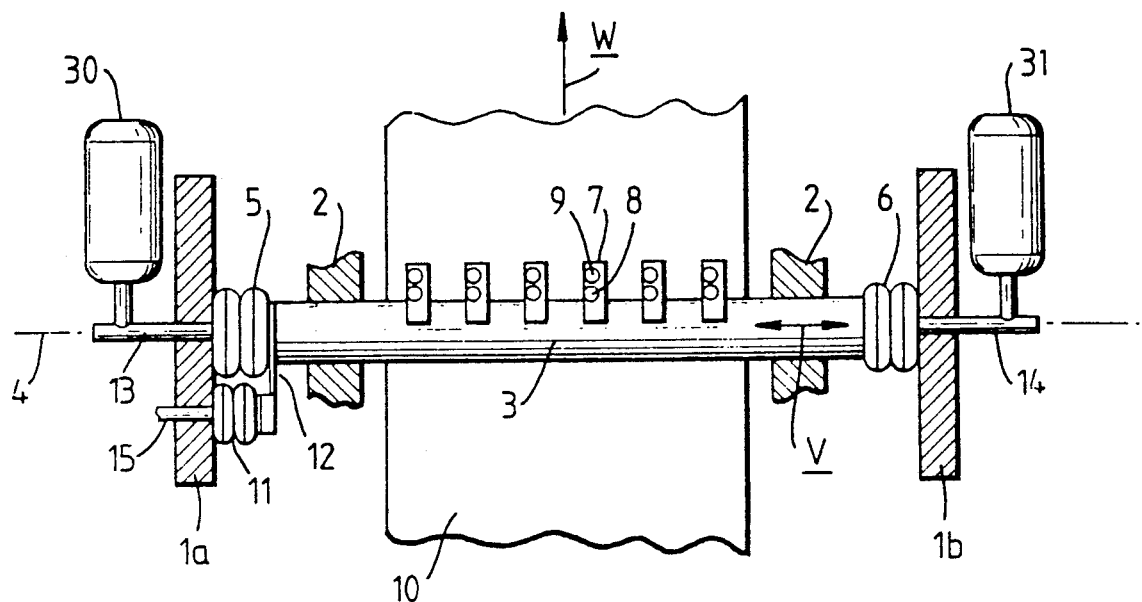
FIG. 1 shows a partially cross-sectional view of a surface testing device, according to the invention, which is operated with pneumatic springs, shown with the structural component parts required for an understanding of the invention.

FIG. 1 shows a surface testing device with supports $1a$, $1b$ and bearings 2 of a base frame. A sensor carrier 3 in the form of a preferably rigid beam is supported in the bearings 2 (e.g. pneumatic bearings) so as to be movable in a reciprocating manner in the direction of a double arrow v and parallel to its longitudinal axis 4. One end of a spring element in the form of a pneumatic spring 5 and 6, respectively, is fastened in each instance at the two ends of the sensor carrier 3, the other end of the spring element being supported and fastened at the supports $1a$, $b$. The two pneumatic springs 5, 6 are pretensioned in the compression direction in such a way that, in the shown rest position, the pneumatic spring 5 tries to press the sensor carrier 3 to the right in the direction of the support $1b$ and, conversely, the pneumatic spring 6 tries to press the sensor carrier 3 to the left in the direction of the support $1a$. The two pneumatic springs 5, 6 accordingly act on the sensor carrier 3 in opposite directions and, with equal pretensioning and equal rigidity (also designated directional quantity), hold the latter in a central, normal zero position between the supports $1a$, $b$. In this zero position, the forces acting from both sides on the sensor carrier 3 are equal, so that with identical construction and coupling of the pneumatic springs 5, 6, the same pneumatic pressure (henceforth designated as "center pressure") also occurs in them. The main active paths of the pneumatic springs 5, 6 preferably extend along the longitudinal axis 4 and parallel to the latter. With respect to the pneumatic springs 5, 6, the normal zero position coincides approximately with the center of that distance which would be covered by their ends connected with the sensor carrier 3 between the extreme allowable compression and extension of the pneumatic springs in the absence of external counterforces. On the other hand, the total travel of the sensor carrier 3 is selected so as to be equal to or somewhat smaller than this distance, so that the pneumatic springs 5, 6 only exert pressure forces on the sensor carrier 3 along the total travel.

At least one holder 7 for a testing sensor 8 is fastened at the sensor carrier 3. A plurality of such holders 7, which can carry a distance sensor 9 in addition to the testing sensors 8 (e.g. crack sensors), are preferably provided along the sensor carrier 3. The sensors 8, 9 are e.g. inductive sensors or sensors operating with eddy currents (DE-OS 20 44 331, DE-OS 27 46 618, DE-OS 33 24 444, U.S. Pat. No. 4,258,319), ultrasonic sensors, laser sensors, or the like, for determining preselected characteristics (thickness, coating qualities, deformations, etc.).

A test piece 10 with the surface to be tested, e.g. a flat steel slab, is arranged under the testing device and can be conveyed in the direction of an arrow w, i.e. vertically relative to the longitudinal axis 4 of the sensor carrier 3, by means of rollers or the like, not shown.

The sensor carrier 3, the pneumatic springs 5 and 6, the holders 7 and the sensors 8 and 9 form a vibratory system whose resonance frequency is a function of the mass of these structural component parts and the directional quantities of the pneumatic springs 5, 6.

An exciter arrangement which comprises at least one additional pneumatic spring 11, e.g. fastened and supported by one end at the support 1a and securely connected by the other end with the sensor carrier 3 via a rigid arm 12, advisably serves to excite the vibratory system. The pneumatic springs 5, 6 can be filled with or emptied of air via connections 13, 14 in order to produce in them a preselected air pressure which remains substantially constant during operation, while the other pneumatic spring 11 is acted upon with compressed air or emptied of air, respectively, via a connection 15 in the cycle of the forced vibration. The devices required for this are explained in the following. The expression "air" naturally also comprehends other gases which are usable for the purposes of the invention.

After a transient effect, the vibratory system (3-9) vibrates in a reciprocating manner at the frequency of the exciter arrangement against the existing friction forces (e.g. air friction) in arrow direction v, wherein the surface of the test piece 10 is tested continuously for cracks or other characteristics by the test sensors 8, while the distance sensors 9 can simultaneously serve to keep the test sensors 8 at a constant distance from the surface to be tested (DE-OS 35 32 654).

The maximum movement travel of the sensor carrier 3 between its reversal points is predetermined by means of the pneumatic springs 5 and 6 used in the individual case and by means of the limiting loads prescribed by the respective manufacturers of such pneumatic springs. Although it would also be possible to use other pneumatic springs, it is preferable for the purposes of the invention to use pneumatic springs 5, 6 which are loaded in compression, but not in tension. Friction-resistant pneumatic springs in the form of bellows comprising rubber or the like are particularly suitable, the latter being provided with mounting plates or the like at their surfaces extending vertically relative to the main active path.

Figure 2:
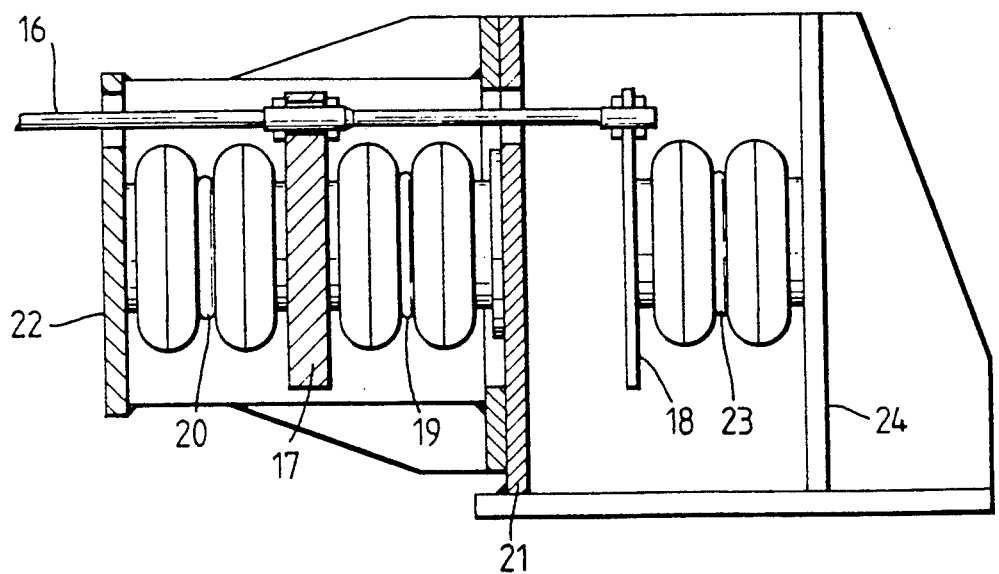
FIG. 2 shows a view, similar to that of FIG. 1, of an alternative embodiment of the invention.

FIG. 2 shows an alternative embodiment form of the invention. A sensor carrier 16 which is supported so as to be displaceable in a base frame in a manner not shown in more detail comprises two arms 17 and 18 which project transversely relative to its longitudinal direction. The arm 17 is supported between one end, respectively, of each pneumatic spring 19, 20, the latter being pretensioned like the pneumatic springs 5, 6 and supported at the frame walls 21, 22 by their other ends. The other arm 18 is connected with one end of another pneumatic spring 23 which acts as an exciter, the other end of the pneumatic spring 23 being supported at a wall 24 of the base frame. The arms 17, 18 are advisably arranged at an end of the sensor carrier 16, but could also be provided in a central portion of same, for example.

Figure 3:
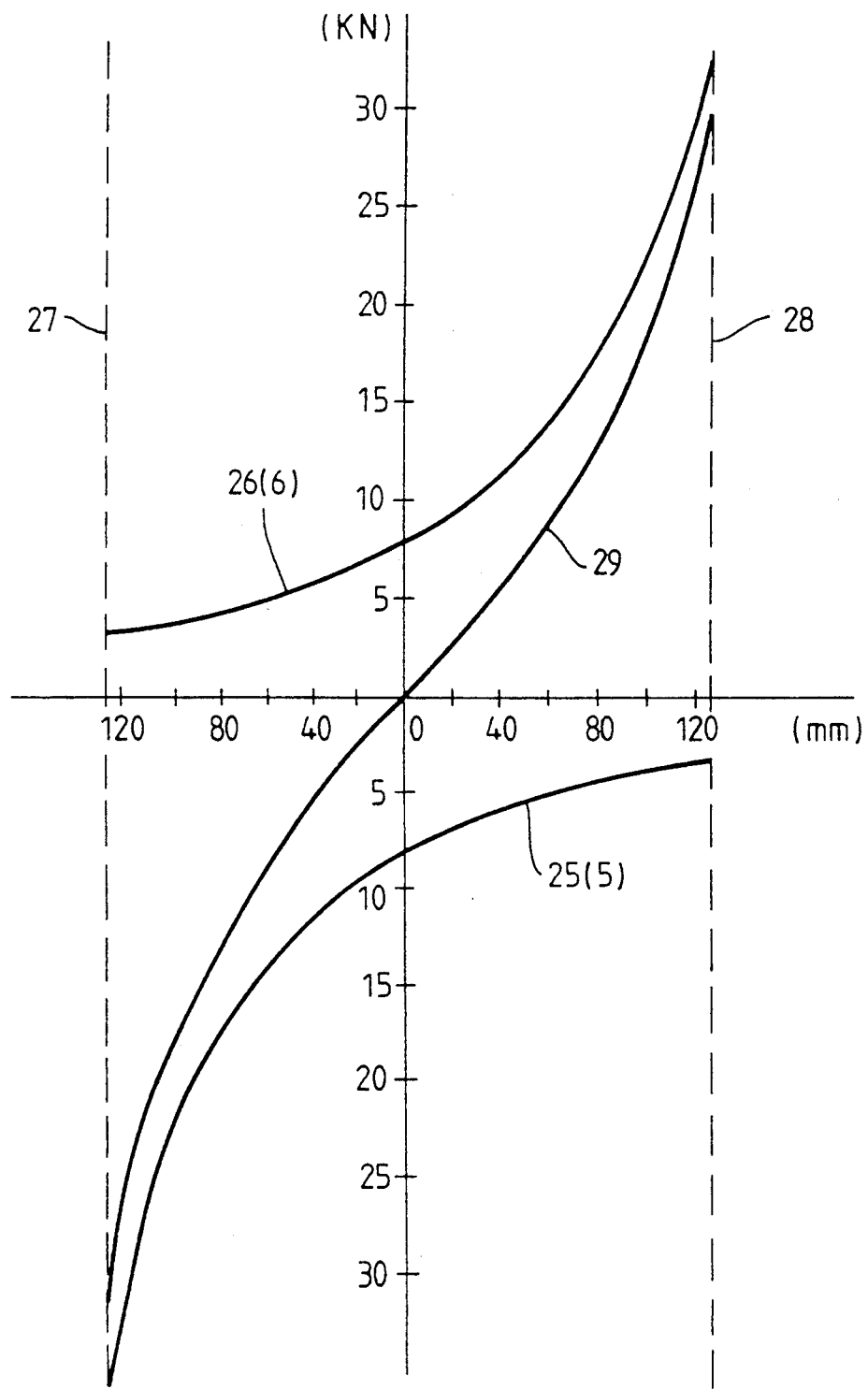
FIG. 3 shows a typical characteristic line of the pneumatic springs according to the invention.

FIG. 3 shows the spring characteristic lines and directional quantities which are obtained when using the pneumatic springs 5, 6 and 19, 20, respectively, according to the invention. The deflection in the compressive direction is plotted along the abscissa in millimeters and the restoring force developed by the pneumatic springs as a result of this deflection is plotted along the ordinate in kilonewtons in a cartesian coordinate system. A curve 25 designates e.g. the characteristic line of the pneumatic spring 5, while the characteristic line of the pneumatic spring 6 is indicated by means of a curve 26. Therefore, in the zero point of the coordinate system, the pneumatic spring 5 exerts a restoring force of approximately $-7.5$ kN on the sensor carrier 3 due to the described pretensioning, which restoring force acts toward the right in FIG. 1, while the pneumatic spring 6 simultaneously acts on the sensor carrier 3 with a restoring force of approximately $+7.5$ kN, which is directed toward the left in FIG. 1, so that the sensor carrier 3 is in equilibrium, i.e. in its normal rest position or zero position. If the sensor carrier 3 oscillates out of this zero position to the right in FIGS. 1 and 3, the restoring force of the pneumatic spring 6 increases corresponding to the curve 26, while the remaining restoring force of the pneumatic spring 5 simultaneously decreases to an increasing extent. During a deflection of approximately 120 mm, the restoring force of the pneumatic spring 6 is very large at approximately 30 kN, the restoring force of the pneumatic spring 5, on the other hand, is still very small at approximately 3 kN. Corresponding ratios with the opposite curve and opposite direction of the restoring forces result during the deflection of the sensor carrier 3 to the left in FIGS. 1 and 3. The possible deflections of the ends of the pneumatic springs in the shown example, which ends are connected with the sensor carrier 3 and can be moved in a reciprocating manner with the latter, are designated by dashed lines 27, 28, a maximum possible movement travel of somewhat less than approximately 250 mm resulting from this for the sensor carrier 3.

The resultant from the characteristic lines 25, 26 is indicated in FIG. 3 by a curve 29 which results from the sums of the respective restoring forces. Accordingly, no resultant restoring force acts on the sensor carrier 3 in the zero position, whereas a resultant restoring force acting toward the left (right) occurs during its deflection to the right (left) in FIGS. 1 and 3.

Figure 4:
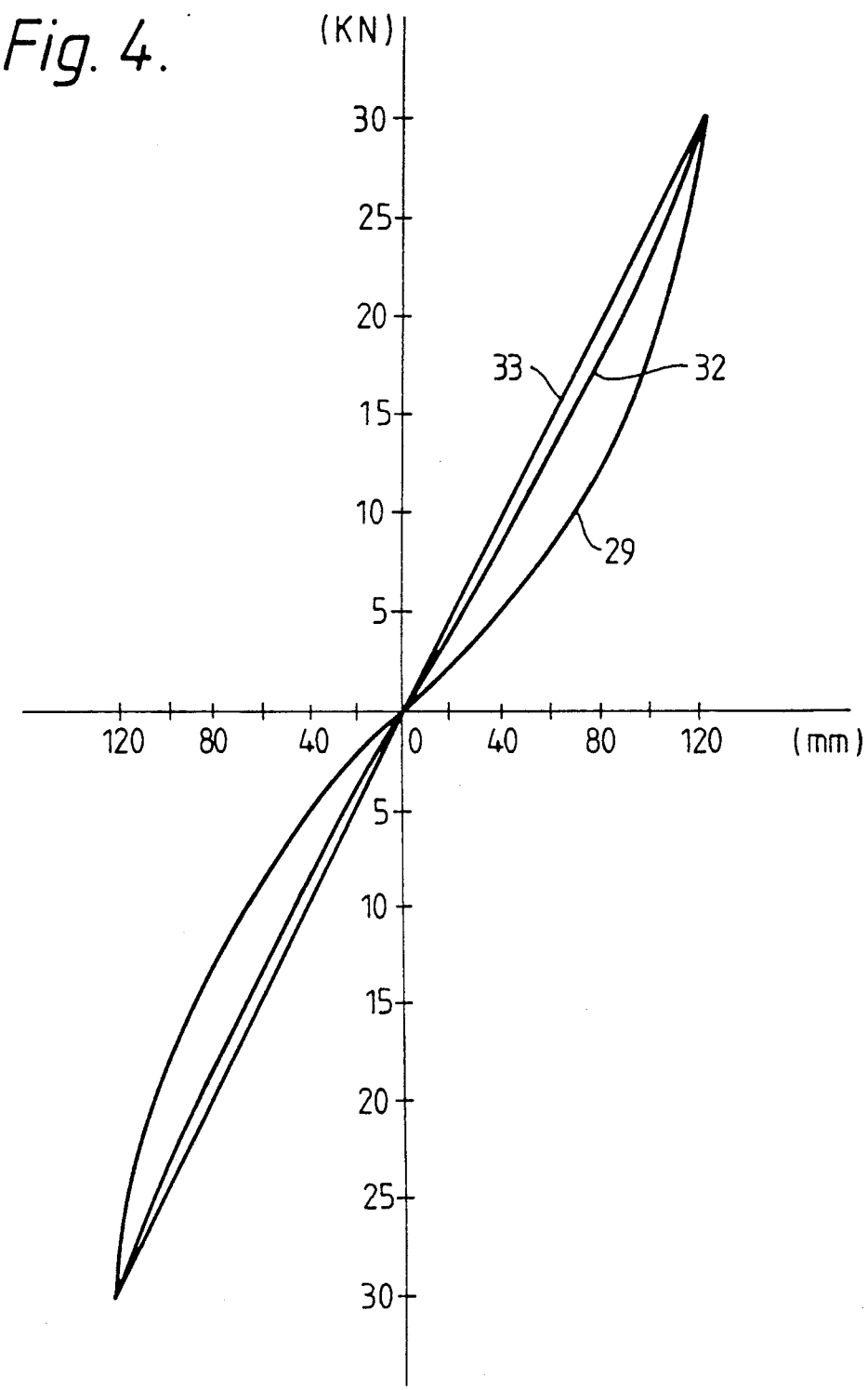
FIG. 4 shows a linearized characteristic line of the pneumatic springs according to the invention.

Since the directional quantity of the spring system formed by the two pneumatic springs 5, 6 and 19, 20, respectively, can be imagined as a slope of the curve 29 which extends only to a great extent in a linear manner, it is variable chiefly at the ends of the tolerated movement travel 27, 28 with the result that a non-harmonic vibration results for the vibratory system. This is sometimes undesirable, since the evaluation of the signals supplied by the sensors 8, 9 is effected in a simpler manner if the vibratory system executes a harmonic sine oscillation, which presupposes a completely linear relationship between the restoring force and the deflection. Such a linear relationship can be obtained, according to the invention, in that the connections 13, 14 are connected, in accordance with flow, with rigid supply reservoirs 30, 31 or containers with adjustable volume which receive an additional air volume which remains constant during the vibrations in contrast to the pneumatic springs 5, 6 and 19, 20, respectively. On the other hand, the result of such additional volumes, particularly if they are of identical dimensions, is, corresponding to FIG. 4, that the originally curved characteristic line corresponding to curve 29 is considerably flattened (curve 32) and the optimal linear curve (curve 33) is approximated to a great extent.

Figure 5:
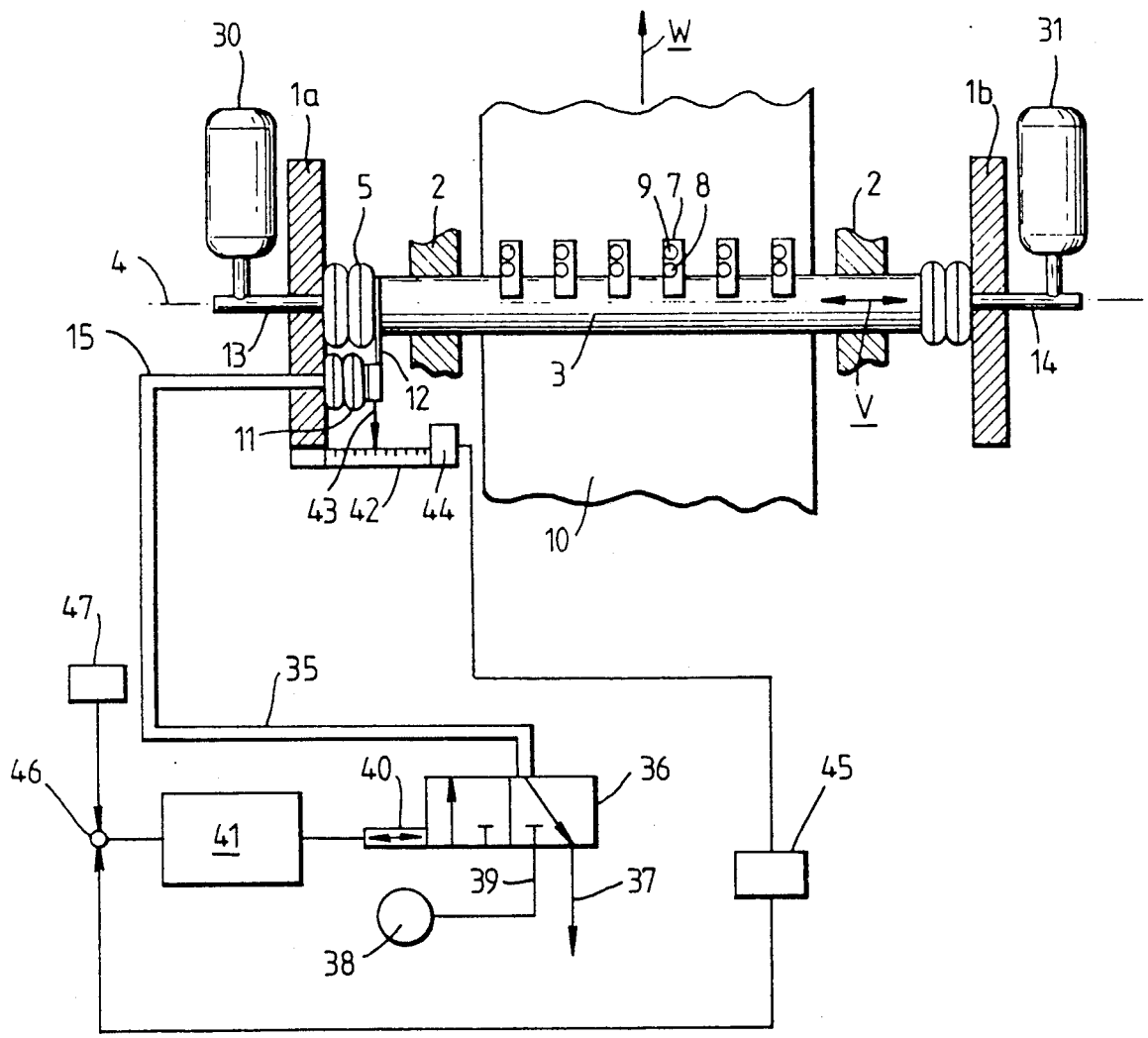
FIG. 5 shows a partially cross-sectional view of an exciter arrangement, according to the invention, for the vibratory system in connection with a control and regulating device for changing the amplitude of the vibratory system.

FIG. 5 shows an exciter arrangement for the vibratory system form of the embodiment according to FIG. 1, although the same exciter arrangement could also be used for the embodiment according to FIG. 2. It is assumed that the connections 13, 14 are closed. The output of a 3/2-way valve 36 is connected with the connection 15 via a conduit 35 and comprises an input leading to open air (de-aerating line 37), and an input which is connected to a pressure line 39 connected with a compressed air source 38, so that the conduit 35 is connected with open air in one valve position and with compressed air source 38 in the other valve position. An electrical control connection 40 of the valve 36 is connected with the output of a regulator 41. For the purpose of measuring the deflection of the pneumatic spring 11, which deflection is preferably effected parallel to arrow v, a path measuring device 42 is provided which likewise acts parallel to arrow v and which senses the respective position of an indicator 43, or the like, by inductive, optical or like means, the indicator 43 being fastened at the end of the pneumatic spring 11 connected with the arm 12 and comprising a converter 44 which transmits an electrical signal at its output corresponding to the respective vibration amplitude of the pneumatic spring 11. This signal is converted by a peak value measuring device 45 during every displacement into a signal indicating the instantaneously achieved amplitude of the indicator 43 or the sensor carrier 3, so that the path measuring device 42 and the peak value measuring device 45 act as an actual value indicator for the amplitude. The generated actual signal is fed to a comparator 46 and compared in the latter with a reference value signal for the amplitude of the pneumatic spring 11 desired in the individual case, the reference value signal being supplied by a reference value transmitter 47. The comparator 46 transmits a signal which corresponds to the difference between the reference value signal and the actual value signal coming from the peak value measuring device 45 and is fed to an input of the regulator 41. The latter transmits, at its output, a regulated signal for the control connection 40 of the valve 36, so that the latter is switched on during every travel of the pneumatic spring 11 until the length of the movement travel is substantially adjusted to the reference value supplied by the reference value transmitter 47. If the natural frequency of the vibratory system (3, 5-9) is e.g. 4 Hz, corresponding to a period of vibration of 250 msec, the valve 36 is switched on, e.g. with the same frequency, for a period of e.g. approximately 30 msec in each instance, and the pneumatic spring 11 is consequently connected with the compressed air source 38 for a corresponding period of time. Subsequent to this, the pneumatic spring 11 is connected again with the external atmosphere, so that exciting force can no longer be transmitted to the vibratory system. In this example, the regulator 41 works in the manner of a pulse width control with an adjustable pulse duty factor which is a function of the respective actual value at the output of the peak value measuring device 45 and the desired reference value. The switch-on times are in advance of the vibration of the vibratory system in a corresponding manner, preferably by approximately 90°.

Alternately, the switch-on of the valve 36 can also be effected with a repetition frequency diverging from the resonance frequency of the vibratory system. However, the excitation of the vibratory system should be effected at least at a frequency in the vicinity of the resonance frequency in order to keep the forces needed for exciting the vibrating masses at a low level.

The pneumatic spring 11 is advisably clamped between the sensor holder 3 and the support 1a in such a way that it is substantially only acted upon by pressure like the pneumatic springs 5, 6 and is therefore deflected to a maximum value resulting from the pressure of the compressed air source 38 in the absence of external forces.

Figure 6:
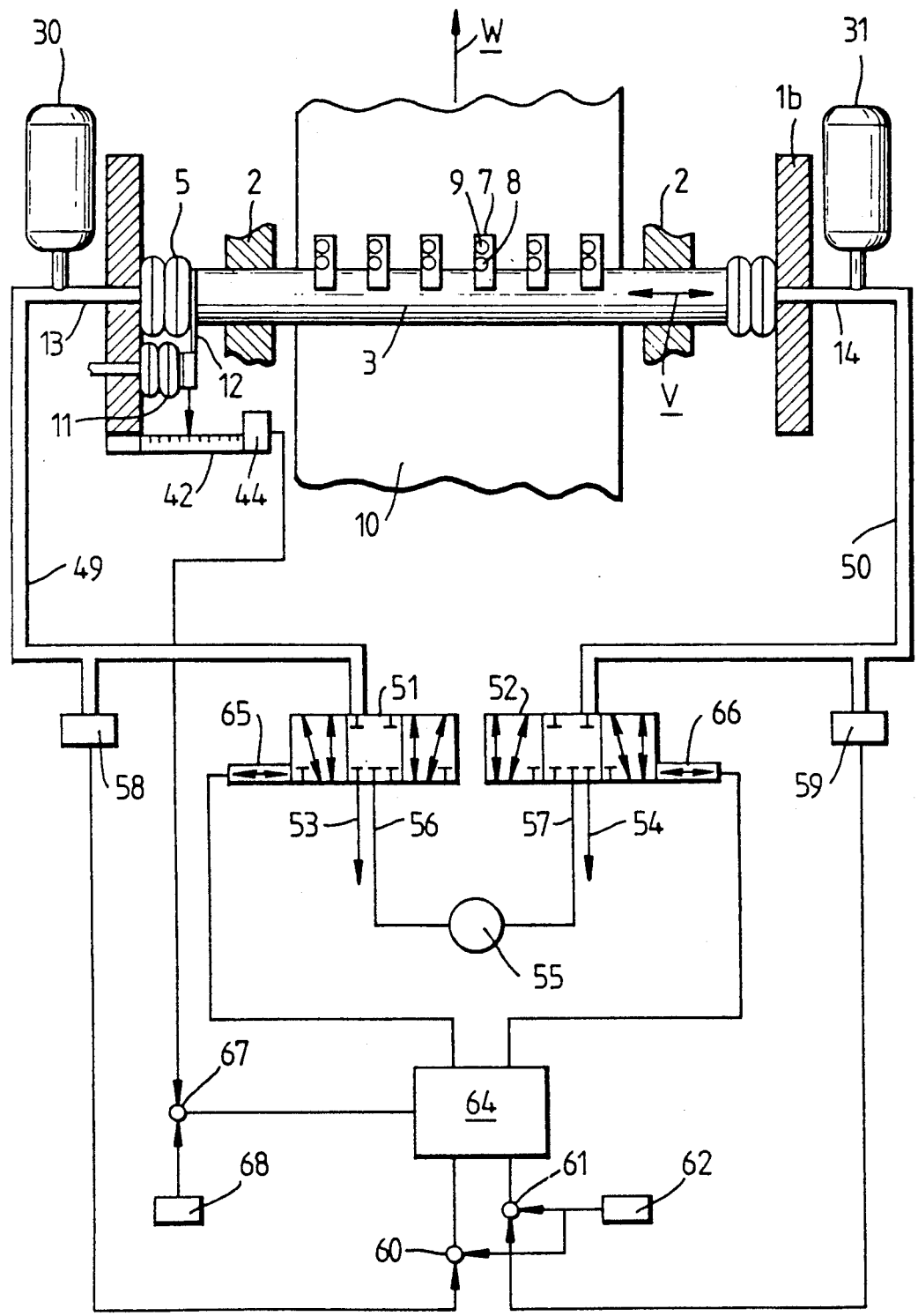
FIG. 6 shows a schematic view of a control, and regulating device, according to the invention, for the testing device for the purpose of changing the natural frequency and/or the zero position of the vibratory system.

FIG. 6 shows devices with which the zero position and the resonance frequency and center pressures, respectively, can be changed in a simple manner. The device of the embodiment according to FIG. 1 can also be used in a corresponding manner in the embodiment according to FIG. 2.

According to FIG. 6, the connections 13, 14 are connected via conduits 49, 50 to the output of a 5/3-way valve 51 and 52, respectively, each output comprising an input (de-aerating lines 53, 54) leading to the external atmosphere and an additional input which is connected to a compressed air source 55 via a pressure line 56, 57 in each instance. Pressure measuring devices 58, 59 (actual value transmitters) are connected in the conduits 49, 50 in each instance and transmit electrical signals at their outputs, which electrical signals correspond to the instantaneous center pressures in the lines 49, 50 and feed them to a comparator 60, 61 whose other input is connected with a reference value transmitter 62 for these center pressures and whose output is connected with a regulator 64. The outputs of this regulator 64 are connected with a control connection 65, 66 of the valves 51, 52 in each instance in order to be able to switch them into one of the three shown positions by means of corresponding control signals.

The conduits 49, 50 are closed in the shown normal position of the valves 51, 52, connected to the de-aerating lines 53, 54 in another position, and connected with the pressure lines 56, 57 in the third position. The path measuring device 42, which was already described with the aid of FIG. 5, is connected with an additional comparator 67, a reference value transmitter 68 for the zero position being connected to the other input of the latter, while its output is connected to an input of the regulator 64. The path measuring device 42 serves in this case as an actual value transmitter for the zero position of the vibratory system.

The described device operates as follows for adjusting and/or changing the resonance frequency of the vibratory system and the center pressure in the pneumatic springs 5, 6.

A reference value for the center pressures of the two pneumatic springs 5, 6 is preselected by the reference value transmitter 62. Since the air located in the pneumatic springs 5, 6 and containers 30, 31, respectively, determines the spring rigidity of the vibratory system and the directional moment, respectively, and the latter is increased by supplying more air or is reduced by removing air, an increase (reduction) of the center pressures in the zero position also results in an increase (reduction) of the resonance frequency of the system.

Moreover, an adjustment or change of the reference value with the reference value transmitter 62 causes the comparators 60, 61 to transmit corresponding differential signals when the center pressures determined by the pressure measuring devices 58, 59 deviate from the adjusted reference value, which differential signals are converted by the regulator 64 into actuating signals for the valves 51, 52, whereupon the latter are moved into one or the other of the two possible positions—proceeding from their position according to FIG. 6—until the air quantities and, accordingly, also the center pressures in the pneumatic springs 5, 6 are increased or reduced in the desired manner.

If a change in the zero position of the sensor carrier 3 is effected with the device according to FIG. 6, i.e. if its position in the rest state or its position in the zero passages in the vibrating state, respectively, is moved to the right or left relative to the normal zero position seen in FIGS. 1 and 3, this device can be constructed and can work in a twofold manner as follows:

In one variant, the air quantity is increased or reduced only in one or the other pneumatic spring 5, 6 by correspondingly adjusting the reference value transmitter 68. A change in the reference value causes a differential signal to be fed to the regulator 64 from the comparator 67 and the regulator 64 then connects one of the conduits 49, 50 to the pressure or de-aerating lines 56, 57 and 53, 54, respectively, via the valves 51, 52 until the desired displacement of the zero position is achieved due to the larger or smaller air quantities in one or the other combination of pneumatic spring 5 and container 30 or pneumatic spring 6 and container 31, respectively. In the vibrating state, the vibratory system then oscillates around this new zero position which e.g. could also be displayed visually by means of the path measuring device 42. The described change in the zero position is, of course, connected with a change in the resonance frequency of the vibratory system, which change is not always desired, since the supply or removal of air on one side also leads to a changed center pressure in the newly adjusted zero position.

Therefore, in order to change the zero position according to the other, preferred variant, the air quantity is increased in one pneumatic spring and simultaneously reduced in the other pneumatic spring in such a way that the same center pressure as in the normal middle position according to FIGS. 1 and 3 prevails in both pneumatic springs 5, 6. Accordingly, it is ensured in a simple manner that the natural frequency of the vibratory system remains constant despite a change in the zero position. Regulation is preferably effected in such a way that differential signals coming from the comparator 67 on the one hand and differential signals coming from the comparators 60, 61 on the other hand are supplied to the regulator 64. The regulator then switches both valves 51, 52 while taking into account the center pressure adjusted at the reference value transmitter 62 in such a way that the air quantity in one combination (e.g. 5, 30) is increased (reduced) and simultaneously reduced (increased) in a corresponding manner in the other combination (e.g. 6, 31) and the resonance frequency of the vibratory system is accordingly held at the value adjusted at the reference value transmitter 62.

The pressure measuring devices 58, 59 and the path measuring device 42 are advisably adjusted in such a way for the described regulation that they transmit a corresponding output signal only during the zero passages of the sensor carrier. But it would also be possible in an alternative manner to assign a computer to the regulator 64, which computer automatically tests the sine-shaped output signals supplied by the pressure measuring devices 58, 59 and the path measuring device 42 for their positive and negative peak values and pictures the required zero position signals as their mean values. The frequencies and zero positions can accordingly also be changed in both instance during the vibration of the system. This is desired, for example, when the middle position of the test piece 10 changes during its transport in the direction of the arrow w.

Commercially available pneumatic springs, such as those previously known e.g. for damping vibrations, for the resilient support of machines, for spring mounting in motor vehicle construction or the like, are preferably used as pneumatic springs 5, 6 and 11. Pneumatic springs of the type FD 1120-30 from the firm Continental-Gummi-Werke AG in D-3000 Hannover (Germany) have so far proven most suitable for the purposes of the invention. They enable vibrations with a double amplitude of 250 mm at 5 Hz and a center pressure of approximately 2 bar in a vibrating mass of 250 kg. Changes in the zero position of the sensor carrier 3 up to approximately ±20 mm are possible. The changes in the characteristic lines of the pneumatic springs caused by such maximum zero position changes are so small that they influence the total characteristic line of the vibratory system only slightly and are insignificant in practice, particularly when corresponding additional volume (container 30, 31) is provided. A reduction of the usable movement travel of the sensor carrier 3 caused by the zero position changes can accordingly be prevented by selecting from the beginning a displacement which is correspondingly smaller than the maximum allowable displacement with reference to the normal zero position according to FIGS. 1 and 3.

The invention is not limited to the described embodiment examples which can be modified in many ways. This applies on the one hand to the types of coupling of the pneumatic springs 5, 6 to the sensor carrier which are shown only by way of example with the aid of FIGS. 1 and 2, and on the other hand to the types of adjustment of the vibration amplitude, natural frequency and the zero position of the vibratory system shown with the aid of FIGS. 5 and 6. It would be possible, for example, to control the valves 36 and also the valves 51, 52 not by pulses of variable width, but by pulses which possess the preselected constant width and to change instead the number of the pulses supplied to the valves. Of course, this would be connected with a high switching frequency for the valves. Manually actuable control devices acting in a corresponding manner could also be provided instead of regulating devices, the valve 36 in FIG. 5 being adjusted by means of these control devices until the vibration amplitude, which is indicated only visually, for example, has been adjusted, or the valves 51 and/or 52 in FIG. 6 are acted upon in such a way that the desired resonance frequency or zero position of the vibratory system results. A frequency meter could be provided in addition for the display of the respective vibration frequencies. Finally, other exciter arrangements than those shown in FIG. 5 can be used, although the latter are particularly advisable.

It is advisable that the compressed air systems which are normally found in factory rooms and which provide a maximum of 5 bar be used as compressed air sources 38, 55. In using the device described in FIGS. 5 and 6 compressed air sources providing a constant pressure may be used. However, in order to allow a certain freedom of play for changes in frequency which may possibly be necessary, it is advisable to work with a lower center pressure of e.g. 2 bar.

The described valves 36, 51 and 52 are to be viewed only as examples. They were selected from commercially available valves, but can also consist of valves adapted to the specific purpose of application.

The invention is also not limited to the use of two pneumatic springs. Rather, with a corresponding dimensioning and arrangement, three, four or more pneumatic springs can also be provided. When using an odd number of pneumatic springs or pneumatic springs of different constructional types, different center pressures can occur in the individual pneumatic springs in the zero position despite restoring forces which are identical in their entirety. Therefore, it may be advisable in such cases that every pneumatic spring be assigned its own reference value transmitter 62 in FIG. 6.

While the invention has been illustrated and described as embodied in a surface testing device, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

I claim:

1. A surface testing device comprising a frame; at least one sensor for testing a surface of a test piece; a carrier for supporting said at least one sensor; and pneumatic spring means for mounting said carrier to said frame and for reciprocating said carrier along a displacement path to thereby provide for reciprocating movement of said at least one sensor over the tested surface of the test piece, said pneumatic spring means having first pneumatic springs acting in opposite directions on said carrier and being pretensioned in a state of rest of said carrier by a magnitude corresponding to at least half of the displacement path of said carrier, said at least one sensor, said carrier, and said first pneumatic springs forming a vibratory system; said surface testing device further comprising exciter means connected to said vibratory system for operating same at least in vicinity of a resonance frequency of said vibratory system.

2. A surface testing device according to claim 1, further comprising container means for pneumatic pressure medium, and connection means communicating said first pneumatic springs with said container means.

3. A surface testing device according to claim 1, wherein said exciter means comprises at least one second pneumatic spring supported between said frame and said carrier, and means for periodic deflection of said at least one second pneumatic spring.

4. A surface testing device according to claim 3, further comprising a device for regulating a vibration amplitude of said vibratory system and including a control valve having two inputs connected with pressure and de-aerating lines, respectively, and an output connected with said at least one second pneumatic spring, a reference value transmitter for preselecting a magnitude of the vibration amplitude of said vibratory system and generating a reference value signal, an actual value transmitter for sensing an instantaneous magnitude of the vibration amplitude and for generating an actual value signal, and a regulator having an output connected with a control connection of said control valve for regulating operation of said control valve in accordance with a difference between the reference value and actual value signals.

5. A surface testing device according to claim 1, further comprising two control valves for controlling pressure in said first pneumatic springs, respectively, and connected each with a pressure line and a de-aerating line, each of said first pneumatic springs comprising a connection connectable with respective pressure and de-aerating lines via a respective one of said two control valves.

6. A surface testing device according to claim 1, further comprising means for adjusting a preselected resonance frequency of said vibratory system.

7. A surface testing device according to claim 6, wherein said adjusting means comprises two control valves each of which has two inputs connected with pressure and de-aerating lines, respectively, and an output connected with a respective one of said first pneumatic spring, at least one set value pressure device for pre-selecting a magnitude of a center pressure in said first pneumatic springs and for generating a set value pressure signal, two pressure measuring devices for determining an instantaneous magnitude of the center pressure in respective ones of said first pneumatic springs and for generating respective actual value pressure signals, and a regulator connected with respective control connections of said two control valves for controlling operation of said two control valves in accordance with a difference between the set value pressure signal and respective actual value pressure signals.

8. A surface testing device according to claim 7, further comprising a reference position transmitter for pre-selecting a zero position of said carrier and for generating a reference position signal, and a path measuring device for determining an instantaneous zero position of said carrier and for generating an instantaneous position signal, said regulator controlling operation of said control valves in accordance with a difference between the reference position and instantaneous position signals.

9. A surface testing device according to claim 1, further comprising means for adjusting a preselected zero position of said sensor carrier.

10. A surface testing device according to claim 9, further comprising two control valves, each of said two control valves including two inputs connected with pressure and de-aerating lines, respectively, one output connected with a respective first pneumatic spring, and one control connection connected with said adjusting means.

* * * * *